United States Patent [19]
Zayhowski

[11] Patent Number: 5,394,413
[45] Date of Patent: Feb. 28, 1995

[54] PASSIVELY Q-SWITCHED PICOSECOND MICROLASER

[75] Inventor: John J. Zayhowski, Pepperell, Mass.

[73] Assignee: Massachusetts Institute of Technology, Cambridge, Mass.

[21] Appl. No.: 206,124

[22] Filed: Mar. 4, 1994

Related U.S. Application Data

[63] Continuation-in-part of Ser. No. 193,781, Feb. 8, 1994, abandoned.

[51] Int. Cl.⁶ .............................................. H01S 3/11
[52] U.S. Cl. ....................................... 372/10; 372/11; 372/21; 372/22
[58] Field of Search ..................... 372/10, 11, 21, 22

[56] References Cited

U.S. PATENT DOCUMENTS

| 4,982,405 | 1/1991 | Zayhowski et al. | 372/10 |
| 5,119,382 | 6/1992 | Kennedy et al. | 372/11 |
| 5,132,977 | 7/1992 | Zayhowski et al. | 372/10 |
| 5,253,102 | 10/1993 | Okazaki | 372/22 |
| 5,315,433 | 5/1994 | Okazaki et al. | 372/22 |

FOREIGN PATENT DOCUMENTS 2266988  11/1993  United Kingdom ................. 372/11

OTHER PUBLICATIONS

Zhou et al., "Monolithic Self-Q-Switched Cr,Nd:YAG Laser", *Optics Letters*, 18(7):511-512 (Apr. 1, 1993).
Zayhowski, et al., "Optimization of Q-Switched Lasers", *IEEE Journal of Quantum Electronics*, 27(9): 2220-2225 (Sep., 1991).
Szabo, et al., "Theory of Laser Giant Pulsing by a Saturable Absorber", *Journal of Applied Physics*, 36(5):1562-1566 (May, 1965).

*Primary Examiner*—Georgia Y. Epps
*Attorney, Agent, or Firm*—Hamilton, Brook, Smith & Reynolds

[57] ABSTRACT

An apparatus and method for a passively Q-switched microlaser for producing high-peak-power pulses of light of extremely short duration are disclosed. The apparatus comprises a gain medium and saturable absorber disposed within a laser cavity. When the cavity is pumped, the saturable absorber prevents the onset of lasing until the inversion density within the cavity reaches a critical value. The length of the cavity, the material parameters, and the reflectivities of the mirrors are selected such that pulses of duration less than about 1 ns and of peak power in excess of about 10 kW are obtained. The invention has application in high-precision optical radar, nonlinear optics, micromachining, microsurgery, robotic vision, and other technologies requiring high-peak-power laser pulses of extremely short duration.

43 Claims, 2 Drawing Sheets

PASSIVELY Q-SWITCHED PICOSECOND MICROLASER

GOVERNMENT SUPPORT

The Government has rights in this invention pursuant to Contract Number F 19628-90-C-0002, awarded by the United States Department of the Air Force.

RELATED APPLICATIONS

This application is a continuation-in-part of U.S. Ser. No. 08/193,781, filed Feb. 8, 1994, abandoned.

BACKGROUND OF THE INVENTION

This invention relates to the field of lasers. Many applications require the generation of extremely short, high-peak-power pulses of light from a laser. (For the purpose of this discussion, extremely short will refer to pulse durations of about 1 ns or less; high peak power will refer to peak powers of about 10 kW or greater.) One method for producing extremely short pulses is to mode lock the laser. In mode locking, several longitudinal modes of a laser are locked together such that a periodic train of extremely short pulses is produced. The period between pulses is the round-trip time of light in the laser cavity, typically 10 ns. Because of the large number of pulses produced each second, even lasers with high average power (10 Watts–100 Watts or greater) cannot produce pulses with high peak powers.

High-peak-power pulses can be produced by Q switching a laser. In Q switching, the "quality" or "Q" of the laser cavity is changed in order to generate a pulse. The size of conventional Q-switched lasers, along with the physics of the device, precludes the production of extremely short pulses.

Extremely short, high-peak-power pulses can be obtained from either Q-switched mode-locked lasers or amplified mode-locked lasers. Both of these approaches require large (typically several feet long), complicated (requiring daily supervision by a qualified laser technician), power-hungry (several kilowatts of electrical power), and therefore expensive devices.

It has recently been shown that coupled-cavity Q-switched microlasers can produce pulses of less than 300 ps duration with peak powers in excess of 25 kW.

Zayhowski, J. J. and Dill III, C., "Diode-Pumped Microchip Lasers Electro-Optically Q-Switched at High Pulse Repetition Rates," *Optics Letters*, Vol. 17, No. 17, 1201–1203, (Apr. 23, 1992).

Thus, picosecond Q-switched microlasers can produce output pulses as short as large mode-locked lasers With peak powers as high as commercially available Q-switched systems. And, the entire device can fit into a package approximately the size of a standard diode-laser package with the possibility of battery-powered operation.

While coupled-cavity Q-switched microlasers outperform larger conventional devices in every way except average power, there is still room for improvement. In order to obtain proper Q-switching of the coupled-cavity microlaser, high-speed high-voltage electronics are required. The size, performance, and power consumption of the electronics limit the size, performance, and power efficiency of the coupled-cavity Q-switched microlaser system. In addition, the performance of the coupled-cavity laser relies on maintaining interferometric control of the relative lengths of the two constituent cavities, placing tight tolerances on the manufacture of the device and on the temperature control of the device during use.

The passively Q-switched microlaser does not require switching electronics, thereby reducing the size and complexity of the total system, and improving the power efficiency. In addition, there is no need for interferometric control of cavity dimensions, simplifying production of the device and greatly relaxing the tolerances on the temperature control of the device during use. The result is a potentially less expensive, smaller, more robust, and more reliable Q-switched system with performance comparable to that of coupled-cavity Q-switched microlasers. With this combination of attributes, passively Q-switched picosecond microlasers are very attractive for a large range of applications including micromachining, microsurgery, high-precision ranging, robotic vision, automated production, environmental monitoring, ionization spectroscopy, and nonlinear frequency generation.

In the current state-of-the-art, passively Q-switched lasers typically have a pulse length of tens of nanoseconds, although recently pulses of 3.5-ns duration have been demonstrated using a miniature laser constructed from a gain medium which simultaneously acts as a saturable absorber, as described in Zhou, S., et al., "Monolithic Self-Q-Switched Cr,Nd:YAG Laser", *Optics Letters*, Vol 18, No. 7, 511–512, (Apr. 1, 1993).

SUMMARY OF THE INVENTION

The device reported by Zhou had a pulsewidth that is more than 3 times the value that would have been obtained if the cavity length, the laser gain, the intracavity saturable loss, and the reflectivity of the mirrors had been properly selected (based on numbers reported in the manuscript). As a result, the peak power obtained (less than 3 kW for a 1-W continuous wave pump) was also significantly less than it could have been. Furthermore, a complete understanding of the interaction of the laser parameters will allow laser designers to select materials and components for diode-pumped passively Q-switched devices which outperform the current state-of-the-art devices in pulsewidth and peak power by more than an order of magnitude.

The present invention is directed to an apparatus and method for obtaining high-peak-power pulses of laser light of extremely short duration through the proper selection of components for a passively Q-switched laser system. The apparatus of the invention comprises a gain medium and a saturable absorber disposed within a resonant cavity. When appropriately pumped, an optical pulse begins to form. During the early stages of the pulse development, the saturable absorber is bleached, increasing the Q of the resonator and resulting in a short optical pulse. The length of the cavity, the laser gain, the intracavity saturable loss, and the reflectivities of the mirrors are selected such that pulses of less than about 1 ns duration are generated with peak powers in excess of 10,000 times the pump power (for example, 10 kW for a 1 W pump).

BRIEF DESCRIPTION OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

Figure 1:
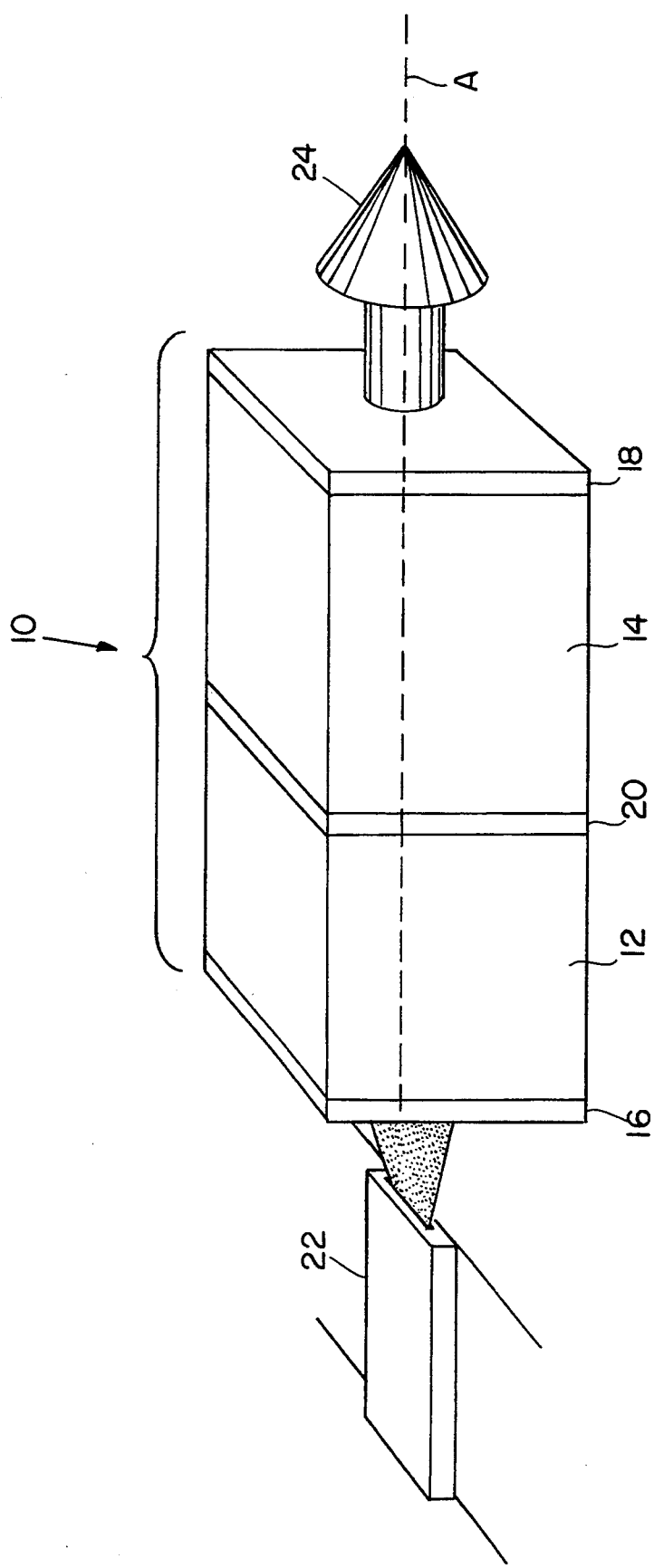
FIG. 1 is a perspective view of a passively Q-switched picosecond microlaser embodying the present invention.

Referring to FIG. 1, one embodiment of the passively Q-switched picosecond microlaser 10 comprises a short piece of gain medium 12, for example $Nd^{3+}$:YAG, bonded to a saturable-absorber crystal 14, for example $Cr^{4+}$:YAG. Both materials are polished flat and parallel on the two faces normal to the optic axis A. The pump-side face 16 of the gain medium 12 is coated dielectrically to transmit the pump light 22 and to be highly reflecting at the oscillating frequency $\nu_1$. The facets at the interface 20 between the gain medium 12 and saturable-absorber crystal 14 are coated dielectrically such that the interface 20 is totally transmitting at the oscillating frequency and highly reflecting at the frequency of the pump 22. The output face 18 of the saturable absorber 14 is coated to be partially reflecting at the oscillating frequency (reflectivity R) and provides the optical output 24 from the device.

The principle behind the operation of the passively Q-switched microlaser 10 is that the saturable absorber 14 prevents the onset of lasing until the average inversion density within the cavity ($N_0$) reaches a value of $$N_0 = \frac{(\gamma_{sat,rt} + \gamma_{par,rt} + \gamma_{op})}{\sigma l_{rt}}, \quad (1)$$

where $\sigma$ is the emission cross section at the oscillating frequency, $l_{rt}$ is the round-trip path length of light within the cavity, $\gamma_{sat,rt} = -\ln(1 - \Gamma_{sat,rt})$ is the round-trip saturable loss constant, $\Gamma_{sat,rt}$ is the round-trip saturable loss, $\gamma_{par,rt} = -\ln(1 - \Gamma_{par,rt})$ is the round-trip unsaturable intracavity parasitic loss constant, $\Gamma_{par,rt}$ is the round-trip unsaturable intracavity parasitic loss, and $\gamma_{op} = -\ln(R)$ is the output-coupling loss constant. The onset of lasing, at this point (inversion density=$N_0$), produces a high intracavity optical field which quickly saturates the saturable component of the loss, increasing the cavity Q and resulting in a Q-switched output pulse. If the cross section of the saturable absorber ($\sigma_{sat} = \gamma_{sat,rt}/N_{sat}l_{rt}$, where $N_{sat}$ is the average density of saturable absorber sites within the cavity) is much greater than the cross section of the lasing transition, then the change in the cavity Q can be modeled as instantaneous. In this case, the minimum possible pulsewidth $$t_w = \frac{5.5 t_{rt}}{\gamma_{sat,rt}}, \quad (2)$$

where $t_{rt}$ is the round-trip time of light within the laser cavity, is obtained when the reflectivity of the output coupler is chosen to be $$R = \exp(\gamma_{par,rt} - \kappa \gamma_{sat,rt}), \quad (3)$$

where $\kappa = 0.47$ (but may vary from 0.0 to 1.5 without changing the pulsewidth by more than a factor of 2). The amount of absorbed pump power required to reach threshold is $$P_{abs,thresh} = \frac{0.74 \pi \gamma_{sat,rt}^2 r_{lm}^2 h\nu_p}{\sigma \tau}, \quad (4)$$

where $r_{lm}$ is the radius of the lasing mode, $h\nu_p$ is the energy of a photon of pump radiation, and $\tau$ is the spontaneous lifetime of the gain medium 12. Once threshold is reached, the invention, when pumped by a diode laser 22, will produce a train of pulses, with the temporal spacing of the pulses given by $$t_p \approx \frac{\tau P_{abs,thresh}}{P_{abs}}, \quad (5)$$

where $P_{abs}$ is the total amount of pump power absorbed within the lasing mode volume.

There are several factors that potentially limit the minimum pulsewidth obtainable from a microlaser. Gain-medium-dependent factors include the maximum inversion density (gain) obtainable for the available pump power and the gain bandwidth. The unsaturable parasitic component of the intracavity loss may make it impossible to realize Equation 3, in which case the required laser efficiency will dictate the choice of output coupler (reflectivity R). Finally, the large optical intensities that result from extremely short pulses may damage the gain medium 12, saturable absorber 14, interface layer 20, or mirrors 16, 18. None of these factors, however, become limiting until the duration of the output pulse from the microlaser is less than several hundred picoseconds. Those skilled in the art will know how to apply Equation 3 subject to these additional restrictions in order to obtain the minimum pulsewidth from a passively Q-switched microlaser.

Figure 2:
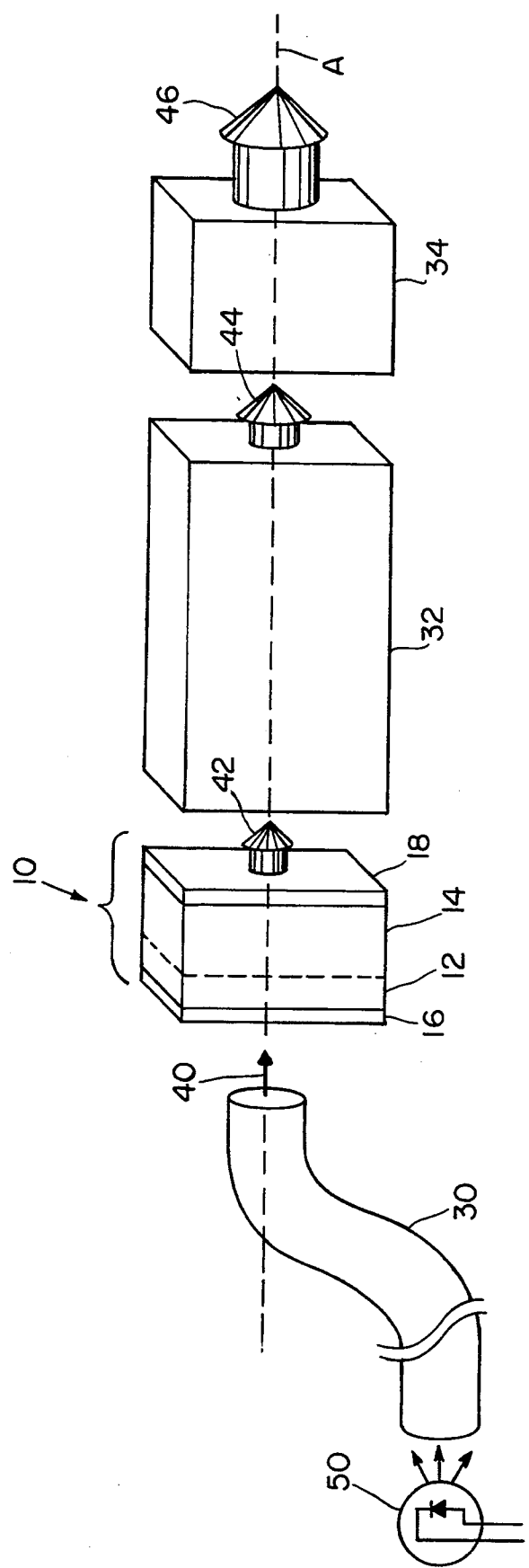
FIG. 2 is a perspective view of a preferred embodiment of the present invention wherein a passively Q-switched picosecond microlaser is pumped by the unfocused output of an optical fiber, and the laser output frequency is quadrupled by a pair of frequency-doubling crystals.

A preferred embodiment of the present invention is shown in FIG. 2, wherein a gain medium 12, for example $Nd^{3+}$:YAG, is diffusion bonded to a saturable-absorber material 14, for example $Cr^{4+}$:YAG. The faces of the combination normal to the optic axis A are polished flat and parallel. The pump-side face 16 of the gain medium 12 is coated dielectrically to transmit pump light 40 and to be highly reflecting at the oscillating frequency $\nu_1$. The output face 18 of the saturable absorber 14 is coated to be partially reflecting at the oscillating frequency (reflectivity R) and provides for laser output 42. The resonant cavity of the laser including both the saturable absorber 14 and the gain medium 12 is preferably of length less than 2 mm.

The output of the optical fiber 30 provides sufficient pump intensity 40 for the laser 10 to reach (and exceed) threshold, without the need for focusing optics. This embodiment lends itself to the generation of extremely short, high-peak-power pulses of light at the remote end of a fiber transmitting low-power continuous wave (cw) light.

A frequency-doubling crystal 32, for example KTP($KTiOPO_4$), is disposed in the path of the laser output beam 42 for generating light 44 at the second harmonic of the oscillating frequency. For example, laser light at an infrared wavelength of 1.064 μm, may be converted by the frequency-doubling crystal into green light at 532 nm.

Frequency-doubling crystals may be stacked for generating light at a frequency which is the fourth harmonic of the laser output 42. A second crystal 34, for example BBO ($\beta$—BaB$_2$O$_4$), is placed adjacent to the first frequency-doubling crystal 32. The laser output 42 is frequency doubled by the first frequency-doubling crystal 32. The output 44 of the first frequency-doubling crystal 32 passes through the second frequency-doubling crystal 34, and is transformed into light 46 at the fourth harmonic of the laser output 42. With this embodiment, diode light 50, transmitted over an optical fiber 30, may be converted by the passively Q-switched picosecond microlaser 10 into laser light 42, which is subsequently quadrupled in frequency by the frequency-doubling crystals 32 and 34 into ultraviolet light 46, which could not be efficiently transmitted using currently available fibers. Thus, ultraviolet light 46 may be generated several kilometers away from a pump diode 50, at the opposite end of a fiber optic cable 30.

The saturable-absorber material 14 and gain medium 12 may both be contained within a common material, as in the case of Nd$^{3+}$, Cr$^{4+}$:YAG. In another embodiment, the saturable-absorber material 14 and gain medium 12 are two different crystals compromised of dopants in a common host, such as Nd$^{3+}$:YAG and Cr$^{4+}$:YAG (where YAG is the common host) and are diffusion-bonded, eliminating the need for an interface dielectric 20. In yet other embodiments, the saturable absorber is epitaxially grown on the gain medium, or the gain medium is epitaxially grown on the saturable absorber. The gain medium may also comprise Nd$^{3+}$:YVO$_4$, while the saturable absorber may comprise LiF:F$_2^-$, a semiconductor material, or a semiconductor-doped-glass material.

If a saturable-absorber material 14 is chosen which is non-absorbing of light at the pump frequency, then the placement of the gain medium 12 and saturable-absorber material 14 may be reversed so that the gain medium 12 is disposed adjacent to the output face 18 and the saturable-absorber material is disposed adjacent to the pump-side face 16.

To illustrate the capabilities of a passively Q-switched microlaser, consider a 0.5-mm-long piece of gain medium 12 comprising Nd$^{3+}$:YAG (gain cross section $\sigma = 4.6 \times 10^{-19}$ cm$^{-2}$ spontaneous lifetime $\tau = 240$ $\mu$s, refractive index n=1.82) bonded to a 0.5-mm-long saturable absorber 14 comprising Cr$^{4+}$:YAG (refractive index n=2.14) with a saturable absorption coefficient of 5.7 cm$^{-1}$. With a lasing-mode radius of 150 $\mu$m, the threshold is $\approx 0.6$ W of absorbed pump power and the pulsewidth is $\approx 100$ ps. If we conservatively assume an efficiency of 10 percent, the pulse energy is 14 $\mu$J, with a peak power of 124 kW (using the theoretical pulse shape) and a peak (unfocused) output intensity of 0.17 GW/cm$^2$. Laboratory experiments using a commercially obtained cw laser diode to pump a passively Q-switched microlaser have already demonstrated pulses of less than 300 ps, with peak powers in excess of 25 kW. The output intensity is sufficient to result in efficient nonlinear frequency generation in an appropriate nonlinear crystal without focussing the output beam of the laser. The focussed peak powers are sufficient for ionization of many materials, with applications in micromachining, microsurgery, and ionization spectroscopy. The extremely short pulses make the device attractive for high-precision optical ranging, with applications in robotic vision and automated production.

While this invention has been particularly shown and described with references to preferred embodiments thereof, it will be understood by those skilled in the art that various changes in form and detail may be made therein without departing from the spirit and scope of the invention as defined by the appended claims.

I claim:

1. A passively Q-switched laser comprising:
    a) a resonant cavity formed between a first mirror and a second mirror;
    b) a gain medium disposed within said resonant cavity for producing laser gain;
    c) a pump source for energizing said gain medium; and
    d) a saturable absorber disposed within said resonant cavity; said saturable absorber, said second mirror, and said laser gain being selected so that output pulses having a duration of less than about 1 nanosecond are generated.

2. The laser of claim 1 wherein said second mirror is an output coupler having reflectivity R, where $$R = \exp(\gamma_{par,rt} - \kappa \gamma_{sat,rt}),$$

$\kappa$ is in the range from 0.0 to 1.5, $\gamma_{sat,rt}$ is the round-trip intracavity saturable loss constant, and $\gamma_{par,rt}$ is the round-trip intracavity unsaturable parasitic loss constant.

3. The laser of claim 1 wherein said gain medium and said saturable absorber are two separate materials comprised of dopants in a common host and wherein said gain medium and said saturable absorber are joined by diffusion bonding.

4. The laser of claim 3 wherein said gain medium is doped with Nd$^{3+}$ and said saturable absorber is doped with Cr$^{3+}$.

5. The laser of claim 3 wherein said host material comprises YAG.

6. The laser of claim 1 wherein said gain medium and said saturable absorber are the same crystal.

7. The laser of claim 1 wherein said gain medium is epitaxially grown on said saturable absorber.

8. The laser of claim 1 wherein said saturable absorber is epitaxially grown on said gain medium.

9. The laser of claim 1 wherein said pump source comprises an optical fiber for transmitting pump light energy; said optical fiber being optically coupled to said first mirror for pumping said gain medium with said light energy.

10. The laser of claim 9 wherein said optical coupling between said optical fiber and said first mirror is without intermediate focussing optics.

11. The laser of claim 1 further comprising nonlinear optical crystals disposed in proximity with said second mirror for frequency conversion of said pulses emitted by said laser.

12. The laser of claim 11 wherein said nonlinear optical crystals comprise a single frequency-doubling crystal.

13. The laser of claim 1 wherein said resonant cavity is less than 2 mm in length.

14. The laser of claim 1 wherein said gain medium comprises a solid-state material.

15. The laser of claim 14 wherein said gain medium is selected from the group consisting of Nd$^{3+}$:YAG and Nd$^{3+}$:YVO$_4$.

16. The laser of claim 1 wherein said saturable absorber comprises a solid-state material.

17. The laser of claim 16 wherein said saturable absorber is selected from the group consisting of $Cr^{4+}$:YAG, $LiF:F_2^-$, a semiconductor material, and a semiconductor-doped-glass material.

18. The laser of claim 1 wherein said mirrors are flat.

19. A passively Q-switched laser comprising:
   a) a resonant cavity formed between a first mirror and a second mirror;
   b) a gain medium disposed within said resonant cavity for producing laser gain;
   c) a laser-diode pump source for energizing said gain medium; and
   d) a saturable absorber disposed within said resonant cavity; said saturable absorber, said second mirror, and said laser gain being selected so that output pulses having a peak power greater than about 10 kilowatts are generated.

20. The laser of claim 19 wherein said second mirror is of reflectivity R, where $$R = \exp(\gamma_{par,rt} - \kappa \gamma_{sat,rt}),$$

$\kappa$ is in the range from 0.0 to 1.5, $\gamma_{sat,rt}$ is the round-trip intracavity saturable loss constant, and $\gamma_{par,rt}$ is the round-trip intracavity unsaturable parasitic loss constant.

21. A passively Q-switched laser comprising:
   a) a resonant cavity formed between a first mirror and a second mirror;
   b) a gain medium disposed within said resonant cavity for producing laser gain;
   e) a laser-diode pump source for energizing said gain medium; and
   d) a saturable absorber disposed within said resonant cavity; said saturable absorber, said second mirror, and said laser gain being selected so that output pulses having a peak power greater than about 10,000 times said laser-diode pump power are generated.

22. The laser of claim 21 wherein said second mirror is of reflectivity R, where $$R = \exp(\gamma_{par,rt} - \kappa \gamma_{sat,rt}),$$

$\kappa$ is in the range from 0.0 to 1.5, $\gamma_{sat,rt}$ is the round-trip intracavity saturable loss constant, and $\gamma_{par,rt}$ is the round-trip intracavity unsaturable parasitic loss constant.

23. A passively Q-switched laser comprising:
   a) a resonant cavity formed between a first mirror and a second mirror; said second mirror having a reflectivity R, where $$R = \exp(\gamma_{par,rt} - \kappa \gamma_{sat,rt}),$$

$\kappa$ is in the range from 0.0 to 1.5, $\gamma_{sat,rt}$ is the round-trip intracavity saturable loss constant, and $\gamma_{par,rt}$ is the round-trip intracavity unsaturable parasitic loss constant;
   b) a gain medium disposed within said resonant cavity for producing laser gain;
   c) a pump source for energizing said gain medium; and
   d) a saturable absorber disposed within said resonant cavity; said saturable absorber preventing the onset of said pulses until the average inversion density within said resonant cavity reaches a value of:

$$N_0 = \frac{\gamma_{sat,rt} + \gamma_{par,rt} + \gamma_{op}}{\sigma l_{rt}}$$

where $N_0$ is the average inversion density, $\sigma$ is the emission cross section at the oscillating frequency, $l_{rt}$ is the round-trip path length of light within the cavity, $\gamma_{sat,rt}$ is the round-trip intracavity saturable loss constant, $\gamma_{par,rt}$ is the round-trip intracavity unsaturable parasitic loss constant, and $\gamma_{op}$ is the output-coupling loss constant.

24. A passively Q-switched laser for producing high-peak-power pulses of light comprising:
   a) a resonant cavity formed between a first mirror and a second mirror;
   b) a gain medium disposed within said resonant cavity for producing laser gain;
   c) a pump source for energizing said gain medium; and
   d) a saturable absorber disposed within said resonant cavity; said saturable absorber, said second mirror, and said laser gain being selected so that output pulses having a duration of less than about 1 nanosecond are generated; said gain medium and said saturable absorber being two separate materials comprised of dopants in a common host; said gain medium and said saturable absorber being bonded by diffusion bonding.

25. A passively Q-switched laser for producing high-peak-power pulses of light comprising:
   a) a resonant cavity formed between a first mirror and a second mirror;
   b) a gain medium disposed within said resonant cavity for producing laser gain;
   c) a laser-diode pump source for energizing said gain medium; and
   d) a saturable absorber disposed within said resonant cavity; said saturable absorber, said second mirror, and said laser gain being selected so that output pulses having a peak power of greater than about 10,000 times said laser-diode pump power are generated; said gain medium and said saturable absorber being two separate materials comprised of dopants in a common host; said gain medium and said saturable absorber being bonded by diffusion bonding.

26. A passively Q-switched laser for producing high-peak-power pulses of light, comprising:
   a) a gain medium having opposed first and second faces for producing laser gain from light emitted by a pump source; said first face being highly transmissive to light emitted from said pump and being highly reflective to light at the lasing wavelength; and
   b) a saturable absorber having opposed first and second faces; said first face of said saturable absorber being disposed adjacent said second face of said gain medium at an interface; said interface being highly transmissive of light at said lasing wavelength; said second face of said saturable absorber having a reflectivity R, where $$R = \exp(\gamma_{par,rt} - \kappa \gamma_{sat,rt}),$$

κ is in the range from 0.0 to 1.5, $\gamma_{sat,rt}$ is the round-trip saturable loss constant, and $\gamma_{par,rt}$ is the round-trip unsaturable parasitic loss constant.

27. The laser of claim 26 wherein said interface between said gain medium and said saturable absorber is highly reflective to light emitted from said pump.

28. The laser of claim 26 wherein said first face of said gain medium and said second face of said saturable absorber are made highly reflective by the deposition of a dielectric coating.

29. A method of forming a passively Q-switched laser comprising the steps of:
   a) forming a resonant cavity between a first mirror and a second mirror;
   b) disposing a gain medium within said resonant cavity for producing laser gain;
   c) energizing said gain medium with a pump source; and
   d) disposing a saturable absorber within said resonant cavity; selecting said saturable absorber, said second mirror, and said laser gain so that output pulses having a duration of less than about 1 nanosecond are generated.

30. The method of claim 29 wherein said second mirror is an output coupler having reflectivity R, where $$R = \exp(\gamma_{par,rt} - \kappa\gamma_{sat,rt}),$$

κ is in the range from 0.0 to 1.5, $\gamma_{sat,rt}$ is the round-trip intracavity saturable loss constant, and $\gamma_{par,rt}$ is the round-trip intracavity unsaturable parasitic loss constant.

31. The method of claim 29 further comprising the step of diffusion bonding said gain medium and said saturable absorber wherein said gain medium and said saturable absorber are two separate materials comprised of dopants in a common host.

32. The method of claim 29 wherein said gain medium and said saturable absorber are the same crystal.

33. The method of claim 29 wherein said gain medium is epitaxially grown on said saturable absorber.

34. The method of claim 29 wherein said saturable absorber is epitaxially grown on said gain medium.

35. The method of claim 29 wherein said pump source comprises an optical fiber for transmitting pump light energy; said optical fiber being optically coupled to said first mirror for pumping said gain medium with said light energy.

36. The method of claim 29 further comprising the step of disposing nonlinear optical crystals in proximity with said second mirror for frequency conversion of said pulses emitted by said laser.

37. A method for forming a passively Q-switched laser comprising the steps of:
   a) forming a resonant cavity between a first mirror and a second mirror;
   b) disposing a gain medium within said resonant cavity for producing laser gain;
   c) energizing said gain medium with a laser-diode pump source; and
   d) disposing a saturable absorber within said resonant cavity; selecting said saturable absorber, said second mirror, and said laser gain so that output pulses having a peak power greater than about 10 kilowatts are generated.

38. The method of claim 37 wherein said second mirror comprises an output coupler having reflectivity R, where $$R = \exp(\gamma_{par,rt} - \kappa\gamma_{sat,rt}),$$

κ is in the range from 0.0 to 1.5, $\gamma_{sat,rt}$ is the round-trip intracavity saturable loss constant, and $\gamma_{par,rt}$ is the round-trip intracavity unsaturable parasitic loss constant.

39. A method for forming a passively Q-switched laser comprising the steps of:
   a) forming a resonant cavity between a first mirror and a second mirror;
   b) disposing a gain medium within said resonant cavity for producing laser gain;
   c) energizing said gain medium with a laser-diode pump source; and
   d) disposing a saturable absorber within said resonant cavity; selecting said saturable absorber, said second mirror, and said laser gain so that output pulses having a peak power greater than about 10,000 times said laser-diode pump power are generated.

40. The method of claim 39 wherein said second mirror comprises an output coupler having reflectivity R, where $$R = \exp(\gamma_{par,rt} - \kappa\gamma_{sat,rt}),$$

κ is in the range from 0.0 to 1.5, $\gamma_{sat,rt}$ is the round-trip intracavity saturable loss constant, and $\gamma_{par,rt}$ is the round-trip intracavity unsaturable parasitic loss constant.

41. A method for forming a passively Q-switched laser for producing high-peak-power pulses of light having extremely short duration comprising the steps of:
   a) forming a gain medium having opposed first and second faces for producing laser gain from light emitted by a pump source; said first face being highly transmissive to light emitted from said pump and being highly reflective to light at the lasing wavelength; and
   b) disposing a saturable absorber having opposed first and second faces adjacent to said gain medium; said first face of said saturable absorber being disposed adjacent to said second face of said gain medium at an interface; said interface being highly transmissive of light at said lasing wavelength; said second face of said saturable absorber having a reflectivity R, where $$R = \exp(\gamma_{par,rt} - \kappa\gamma_{sat,rt}),$$

κ is in the range from 0.0 to 1.5, $\gamma_{sat,rt}$ is the round-trip saturable loss constant, and $\gamma_{par,rt}$ is the round-trip unsaturable parasitic loss constant.

42. The method of claim 41 wherein said interface between said gain medium and said saturable absorber is highly reflective to light emitted from said pump.

43. The method of claim 41 wherein said first face of said gain medium and said second face of said saturable absorber are made highly reflective by the deposition of a dielectric coating.

* * * * *